(12) United States Patent
Beck (10) Patent No.: US 8,216,201 B2
(45) Date of Patent: Jul. 10, 2012

(54) WASHABLE DIAPER AND METHOD OF ASSEMBLY

(76) Inventor: Sandra C. Beck, Rensselaer, NY (US)

( * ) Notice: Subject to any disclaimer, the term of this patent is extended or adjusted under 35 U.S.C. 154(b) by 490 days.

(21) Appl. No.: 12/469,357

(22) Filed: May 20, 2009

(65) Prior Publication Data

US 2010/0298801 A1    Nov. 25, 2010

(51) Int. Cl.
    *A61F 13/15* (2006.01)
(52) U.S. Cl. ......... 604/385.14; 604/385.15; 604/385.16; 604/385.101; 604/385.11
(58) Field of Classification Search ............ 604/385.14, 604/385.15, 385.16, 385.18, 385.101, 385.11
    See application file for complete search history.

(56) References Cited

U.S. PATENT DOCUMENTS

| | | |
|---|---|---|
| 1,979,899 A | 11/1934 | O'Brien et al. |
| 3,658,064 A | 4/1972 | Pociluyko |
| 3,667,466 A | 6/1972 | Ralph |
| 3,794,038 A | 2/1974 | Buell |
| 3,842,838 A | 10/1974 | Gellert |
| 3,936,890 A | 2/1976 | Oberstein |
| 4,955,880 A | 9/1990 | Rodriquez |
| 5,207,662 A | 5/1993 | James |
| 5,217,447 A | 6/1993 | Gagnon |
| 5,221,277 A | 6/1993 | Beplate |
| 5,360,422 A | 11/1994 | Brownlee et al. |
| 5,403,303 A | 4/1995 | Beplate |
| 5,405,342 A | 4/1995 | Roessler et al. |
| 5,458,591 A | 10/1995 | Roessler et al. |
| 5,476,457 A | 12/1995 | Roessler et al. |
| 5,613,959 A | 3/1997 | Roessler et al. |
| 5,891,122 A | 4/1999 | Coates |
| 6,623,466 B1 | 9/2003 | Richardson |
| 6,926,705 B1 | 8/2005 | Coates |
| 2006/0247599 A1 | 11/2006 | Mullen et al. |

FOREIGN PATENT DOCUMENTS

| | | |
|---|---|---|
| DE | 10303903 A1 | 11/2003 |
| GB | 9212147.4 A | 12/1992 |
| WO | 95/10992 A1 | 4/1995 |

OTHER PUBLICATIONS

International Search Report and Written Opinion for corresponding PCT application No. PCT/US2010/035544 mailed on Nov. 3, 2010.
International Preliminary Report on Patentability (IPRP) for corresponding PCT application No. PCT/US2010/035544, mailed Dec. 1, 2011.

*Primary Examiner* — Jacqueline F. Stephens
(74) *Attorney, Agent, or Firm* — Heslin Rothenberg Farley & Mesiti P.C.

(57) ABSTRACT

A washable diaper having an outer article with an inner liner system detachably coupled to the outer article. The outer article has front and back ends, with opposing side edges connecting the ends, and inner and outer surfaces, with at least one fastening mechanism on the inner surface proximate to at least one of the ends. The inner liner system has first and second ends and includes at least one washable article, so that when assembled with the outer article, the first and second ends of the inner liner system align with the front and back ends of the outer article to be detachably coupled. The inner liner system may also include a liner member and/or at least one absorbent pad, configured to be placed within the washable article. A method of assembly of the washable diaper having an outer article and inner lining system is also disclosed.

38 Claims, 8 Drawing Sheets

WASHABLE DIAPER AND METHOD OF ASSEMBLY

FIELD OF INVENTION

The invention relates generally to diapers. More particularly, the present invention relates to washable and reusable diapers.

BACKGROUND OF INVENTION

Disposable diapers and cloth diapers for the absorption and containment of urine and other bodily excrements are generally known in the art. Disposable diapers have been convenient, but are costly and present environmentally adverse consequences.

Cloth diapers with flushable components have been developed, but continue to be inconvenient, bulky, and present unsanitary conditions because of inadequate construction of the diaper. Cloth diapers are often used in conjunction with waterproof plastic pants to provide some protection against leakage. Unfortunately, adding this additional element does not generally solve the longstanding waste constraint and disposal difficulties.

BRIEF SUMMARY OF THE INVENTION

The present invention provides a solution to these identified problems. The present invention provides a durable washable diaper with the convenience and effectiveness of a traditional disposable diaper without the adverse environmental consequences. Consumers will save money and reduce consumer waste because the washable diaper and the absorbent articles are reusable. The liquid pervious liner of the inner liner system, captures any non-liquid waste and is easily removable in its entirety and disposed through a regular toilet. The option of the immediate disposal of solid bodily waste provides increased sanitary conditions.

The present invention provides in one aspect, a washable diaper that has an outer article with a front end and a back end, and opposing side edges connecting the ends. The outer article further has an inner surface and an outer surface with at least one fastening mechanism located on the inner surface and positioned in close approximation to the front or back ends. The washable diaper also has an inner liner system that includes at least one washable article that has a first end and a second end, and is positioned adjacent to the inner surface of the outer article. When the inner liner system is assembled, the first end is aligned to detachably couple to the front end of the outer article and the second end is aligned to detachably couple to the back end of the outer article.

The present invention provides in another aspect, a diaper that has a reusable outer article with a front end and a back end, with opposing side edges extending between the front end and the back end. The reusable outer article also has an inner surface and an outer surface, and has fastening mechanisms positioned on the inner surface of each of the front end and the back end. The diaper also has an inner liner system that includes a washable article with a first end and a second end and is positioned adjacent to the inner surface of the reusable outer article. When assembled with the reusable outer article, the first end of the washable article is aligned and detachably coupled with the front end of the reusable outer article, and the second end of the washable article is aligned and detachably coupled with the back end of the reusable outer article. The inner liner system also includes a flushable liner member that is configured to surround the washable article and be positioned adjacent to the inner surface of the reusable outer article upon assembly of the diaper.

Also described herein is a method of assembling a washable diaper. The method includes the step of obtaining a reusable outer article, that has a front end and a back end, with opposing side edges connecting the front end to the back end, and that also has an inner surface and an outer surface, with a fastening mechanism on the inner surface of each of the front end and the back end. The method may also include the step of obtaining at least one washable article with a first end and a second end. The method may further include the step of obtaining a disposable liner member, with a first end and a second end and configured to cover the washable article. The method may include the step of aligning the first end of the at least one washable article with the first end of the liner member and aligning the second end of the at least one washable article with the second end of the liner member, and wrapping the liner member about the at least one washable article so that the liner member wholly surrounds the at least one washable article forming an inner liner system that has a first end and a second end. The method may further still include the step of positioning the assembled inner liner system within the reusable outer article and securing the inner liner system within the reusable outer article with the fastening mechanisms.

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION FOR CARRYING OUT THE INVENTION

The following detailed description of a washable diaper illustrates by way of example and not by way of limitation. While the detailed description is made in the context of a diaper, it is apparent that the present invention would also be suitable for feminine care products, incontinence garments, training pants, and the like. Generally stated, disclosed herein is an embodiment of a washable diaper, comprising of an outer article and an inner liner system. Further described herein is a method of assembling an embodiment of the washable diaper.

Figure 1:
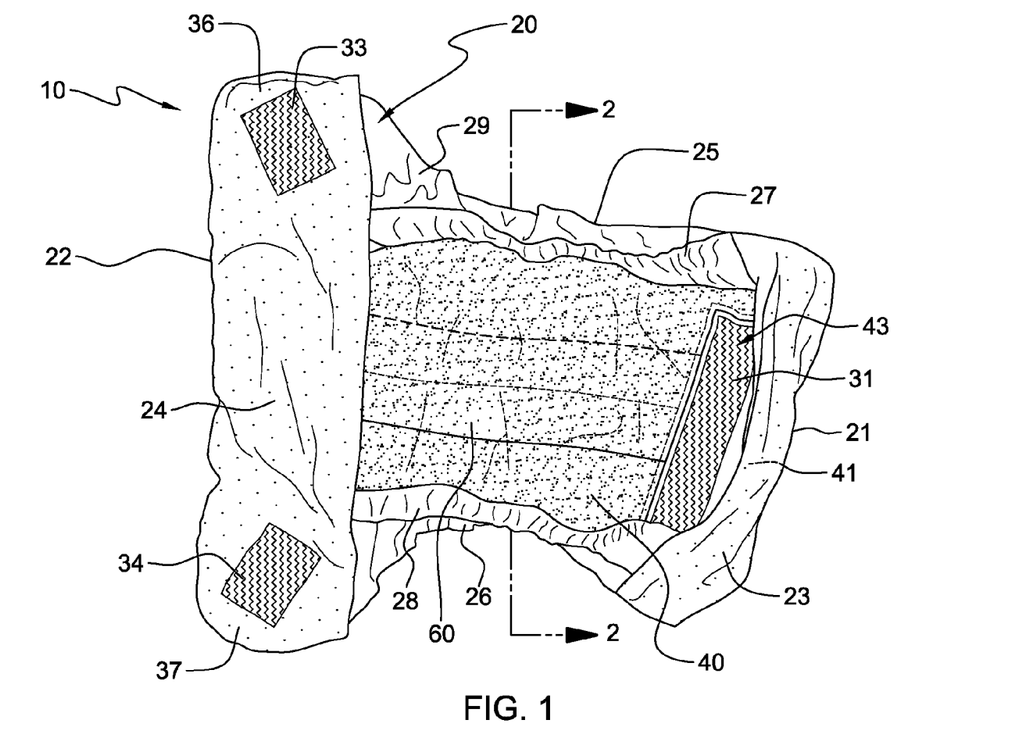
FIG. 1 is a top plan view of one embodiment of a washable diaper, showing an assembled inner liner system detachably coupled to an outer article, in accordance with an aspect of the present invention.

One embodiment of a washable diaper 10, embodying the principles and concepts of the present invention, is illustrated in FIGS. 1-9 and described below. FIG. 1 shows washable diaper 10 that has been assembled, comprising an outer article 20, and an inner liner system 40.

Figure 5:
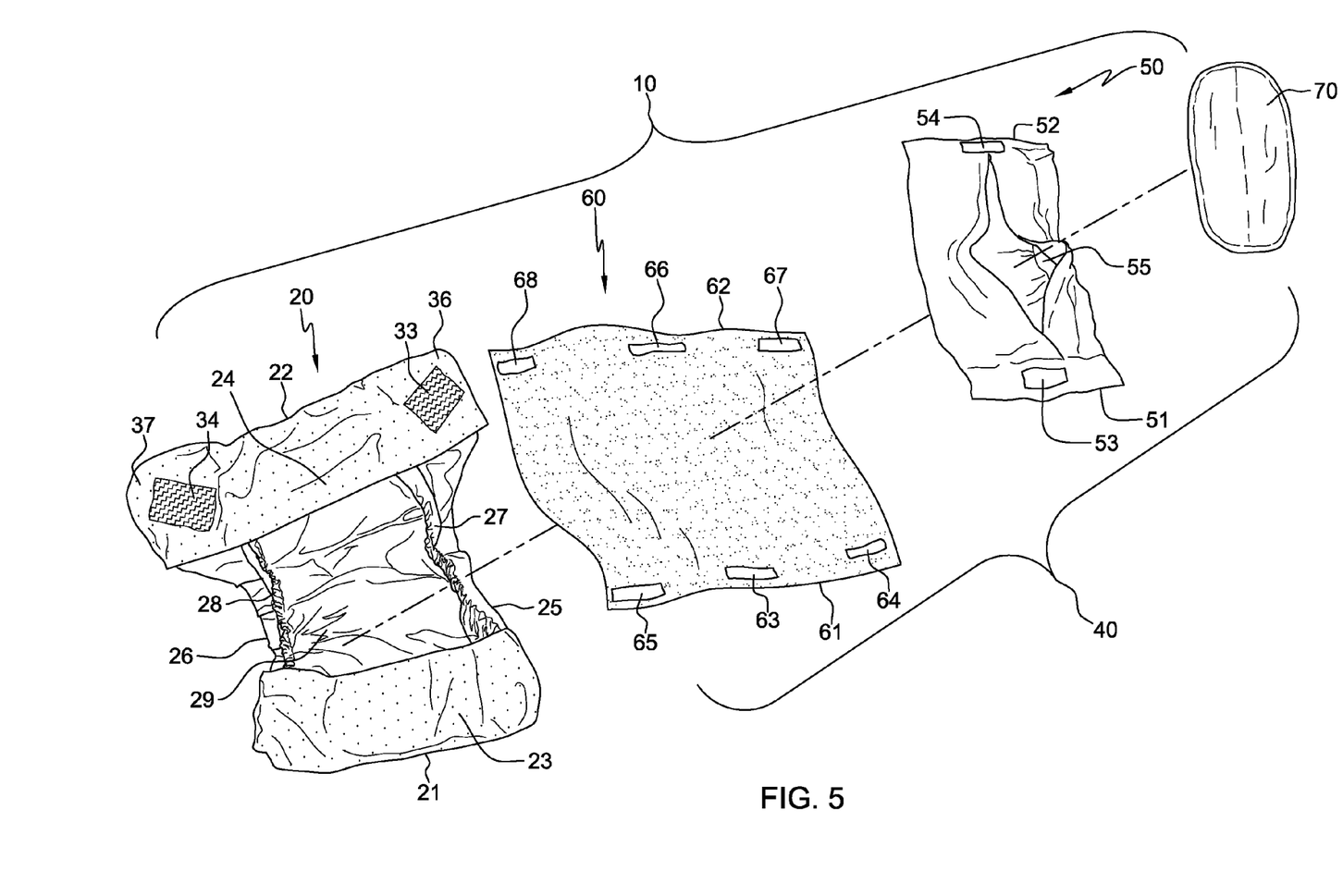
FIG. 5 is an exploded perspective view of the washable diaper of FIG. 1, showing the outer article, the inner liner system that includes a flushable liner, one washable article, and one absorbent pad, in accordance with an aspect of the present invention.

As illustrated in FIG. 5, one embodiment of washable diaper 10 may be assembled with at least one absorbent pad 70, at least one washable article 50, a liner member 60 and outer article 20. At least one absorbent pad 70 is fabricated from any absorbent material, including but not limited to, cotton, flannel, and organic cotton. At least one absorbent pad 70 may further be shaped to better suit the needs of male wearers or female wearers. In assembling washable diaper 10, at least one absorbent pad 70 is inserted within at least one washable article 50, through an opening 55 configured to accept at least one absorbent pad 70.

As seen in FIG. 5, at least one washable article 50 has a first end 51 and a second end 52, and also includes an opening 53 located about first end 51 and an opening 54 located about second end 52. Openings 53, 54 are located on opposing ends of at least one washable article 50. At least one washable article 50 further comprises opening 55 that is configured to receive at least one absorbent pad 70. Opening 55 is disposed on at least one washable article 50 and may be configured to extend longitudinally from first end 51 to second end 52 of washable article 50, and may be located in various positions, including on the front side, back side, or either lateral sides of at least one washable article 50, so long as opening 55 can accommodate the insertion of at least one absorbent pad 70. At least one washable article 50 is typically fabricated from any absorbent material, including, but not limited to, cotton, flannel, and organic cotton.

Figure 6A:
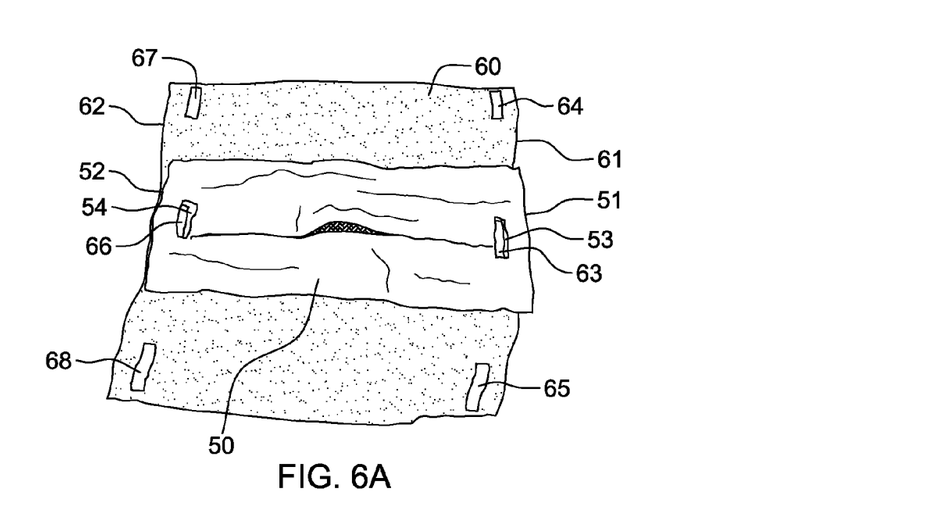
FIG. 6A is a top plan view of the inner liner system that includes the flushable liner and at least one washable article being aligned for assembly, in accordance with an aspect of the present invention.
Figure 6B:
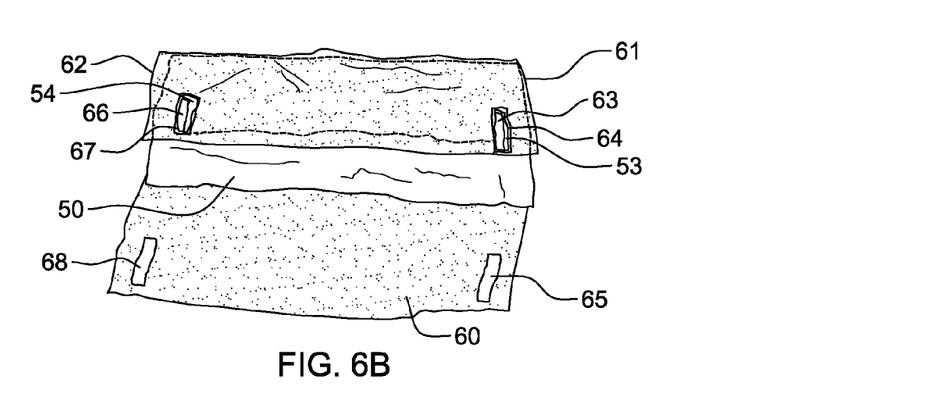
FIG. 6B is a top plan view of the flushable liner and at least one washable article, with one edge of the flushable liner folded over to cover the at least one washable article, in accordance with an aspect of the present invention.
Figure 6C:
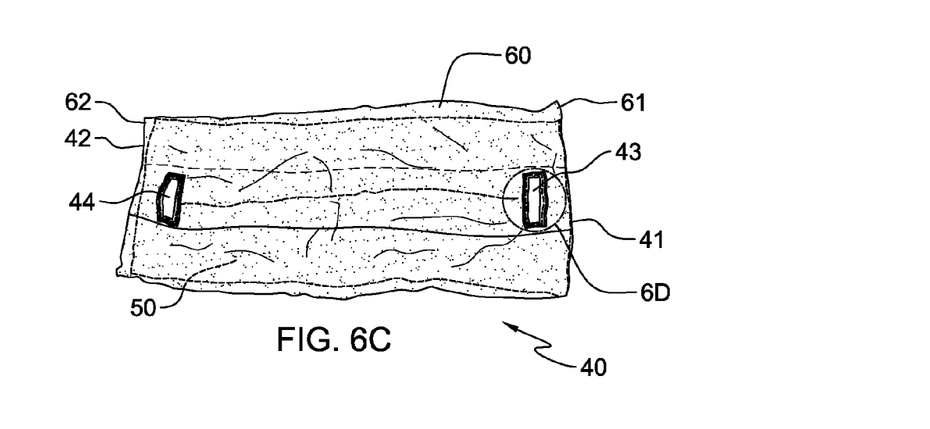
FIG. 6C is a top plan view of the assembled inner liner system that includes the flushable liner and at least one washable article, aligned for assembly with the outer article and with both edges of the flushable liner folded over to cover the at least one washable article, in accordance with an aspect of the present invention.

As exhibited in FIGS. 6A-6C, at least one washable article 50, that may have at least one absorbent pad 70 placed within, is wrapped by or enclosed within liner member 60. Liner member 60, having a first end 61 and a second end 62, has at least one opening 63 on first end 61 and at least one opening 66 on second end 62. Liner member 60 is compliant, soft feeling, and non-irritant to the wearer's skin. Liner member 60 may be fabricated from a liquid pervious material, including but not limited to, rice paper, cellulose fibers, blend of rayon and cellulose fibers and any other liquid permeable hydrophobic fibrous materials that will allow liquid to readily penetrate through its thickness. Liner member 60 may also be fabricated from a material that will wick moisture away from the wearer's skin. Liner member 60 may further still be fabricated from a material that is biodegradable and flushable through a regular toilet system. A person having ordinary skill in the art is aware of the type of liquid pervious material that can be used to manufacture liner member 60 so that it would be biodegradable and flushable. When liner member 60 is fabricated from a liquid pervious, flushable material, it will function to contain non-liquid bodily excrements and allow for easy disposal via a regular septic/sewer system.

Figure 6D:
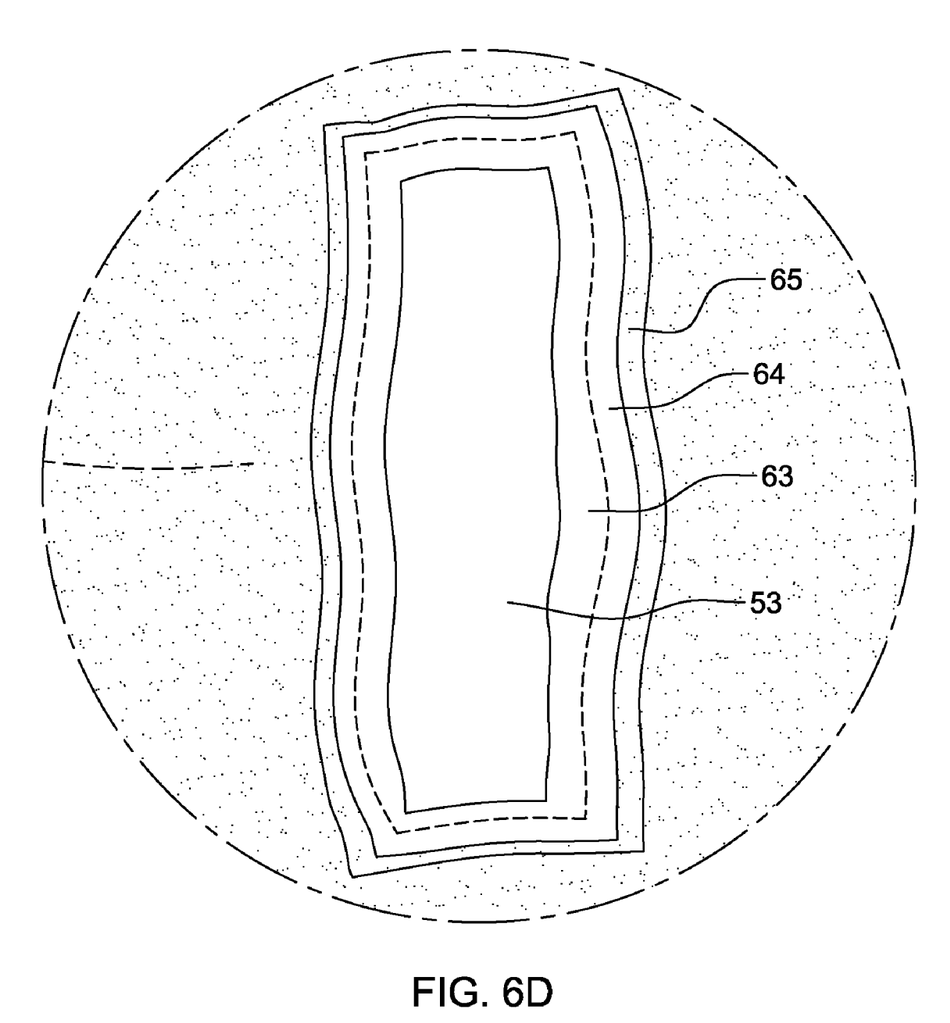
FIG. 6D is an enlarged top plan view, showing the opening at one end of the assembled inner liner system created by aligning the openings of the flushable liner and at least one washable article, in accordance with an aspect of the present invention.

As shown in FIG. 6A, liner member 60 has a length that is approximately the same as at least one washable article 50 and width that is generally wider than at least one washable article 50. Liner member 60 further has three openings 63, 64, 65 on first end 61 and three openings 66, 67, 68 on second end 62. As shown in FIG. 6C, assembled inner liner system 40 has an opening 43 at the first end 41 and an opening 44 at the second end 42. As shown in FIG. 6D, openings 63, 64, 65 on first end 61 of liner member 60 are coaxially aligned with opening 53 on first end 51 of at least one washable article 50 to form opening 43 (shown in FIG. 6C) at first end 41 inner liner system 40.

FIG. 5 shows inner liner system 40 being constructed of at least one absorbent pad 70 placed within at least one washable article 50 and liner member 60. Inner liner system 40 is then configured to detachably couple to outer article 20 by aligning inner liner system 40 adjacent to the inner surface 29 of outer article 20 and, by using the at least one fastening mechanism 31 disposed on the inner surface of the front end 21 (shown in FIG. 1) and the at least one fastening mechanism 32 disposed on the inner surface of the back end 22 (shown in FIG. 7) of outer article 20.

As seen in FIG. 1, first end 41 of inner liner system 40 is aligned with front end 21 and is positioned to be held within the front compartment 23 of outer article 20. Front compartment 23 is configured to receive first end 41 of inner liner system 40 and at least one fastening mechanism 31 detachably couples first end 41 of inner liner system 40 to outer article 20 by coupling opening 43. As also shown in FIG. 1, at least one fastening mechanism 31 is located on front end 21 and is disposed on the inner surface of front compartment 23 of outer article 20 and may be constructed by using hook and loop fasteners, such as the Velcro® brand hook and loop fastener system, but at least one fastening mechanism 31 may also be constructed by using a hook and eye, pin, button, snap button or clasp mechanisms.

Figure 7:
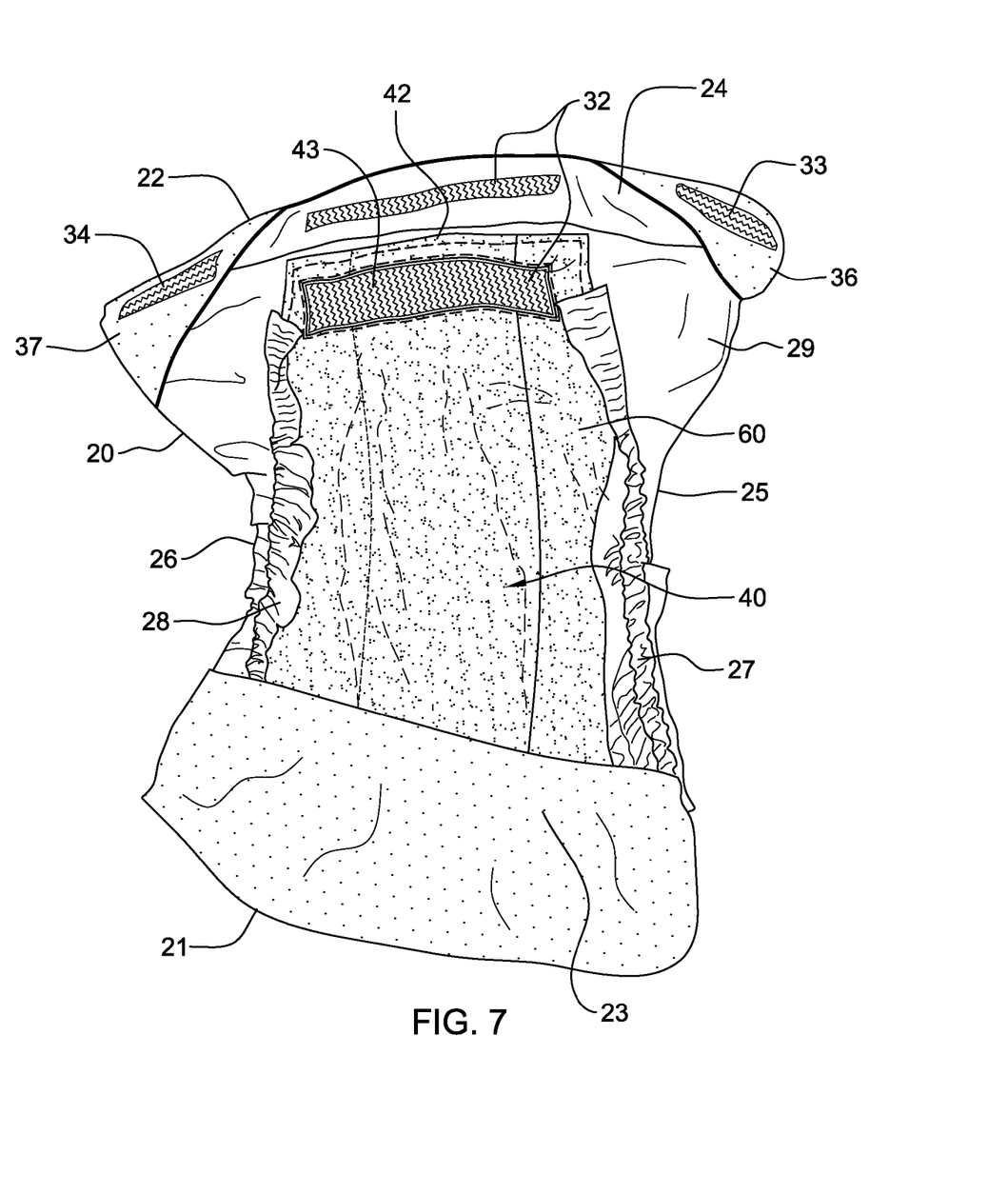
FIG. 7 is a perspective view of the washable diaper of FIG. 1, showing the inner surface of the back end of the outer article and the back compartment, illustrating the fastening mechanism detachably coupling one end of the inner liner system to the back end of the outer article, in accordance with an aspect of the present invention.

As shown in FIG. 7, second end 42 of inner liner system 40 is aligned with back end 22 and is positioned to be held within the back compartment 24 of outer article 20. Back compartment 24 is configured to receive second end 42 of inner liner system 40 and at least one fastening mechanism 32 detachably couples second end 42 of inner liner system 40 to outer article 20. As also exhibited in FIG. 7, at least one fastening mechanism 32 is disposed on the inner surface of back compartment 24 of outer article 20 and may be constructed using hook and loop fasteners, such as the Velcro® brand hook and loop fastener system, but at least one fastening mechanism 32 may also be constructed by using a hook and eye, pin, button, snap button or clasp mechanisms.

As illustrated in FIGS. 1, 5 and 7, outer article 20 is configured with front end 21 and back end 22, and the opposing side edges 25, 26. Outer article 20 may also include the opposing side barriers 27, 28, situated on inner surface 29 of outer article 20 and positioned substantially parallel to opposing side edges 25, 26. As shown in FIGS. 1, 2, 5, and 7, opposing side barriers 27, 28 may be elasticized.

FIGS. 1, 3, 4, 5 and 7 illustrate opposing side edges 25, 26 being configured to conform to the legs of the wearer to maximize fit and minimize potential leakage. This configuration gives outer article 20 an hourglass-like silhouette, with back end 22 being wider than front end 21 due to the extended portions 36, 37 of back end 22. Outer article 20 has back compartment 24, extending perpendicular to opposing sides edges 25, 26, that will allow extended portions 36, 37 to wrap around the wearer's body from the back side to the front side, as seen in FIG. 9. Outer article 20 also has front compartment 23, extending relatively perpendicular to opposing side edges 25, 26, that will allow wrapping around the wearer's body on the front side, as seen in FIG. 8.

In this embodiment of washable diaper 10, front compartment 23 and back compartment 24 are fashioned as a pocket or enclosure like structure, as illustrated in FIGS. 1, 3, 4, 5, and 7, but front compartment 23 and/or back compartment 24 may be designed as a flap, a pouch, reinforced patch of material or reinforced strip of material.

Outer article 20, as shown in FIGS. 1, 3, 4, 5, and 7-9, may be constructed using any material that will allow inner surface 29 (as shown in FIGS. 3, 4, 5 and 7) of outer article 20 to be liquid impervious. Outer article 20 may be comprised of a single layer shell construct manufactured from a liquid impervious material, or liquid resistant material, including but not limited to nylon. Outer article 20 may also be constructed using multiple layers of material, with one layer being constructed of a liquid impervious layer. When outer article 20 is made of multiple layers, a liquid impervious layer may be disposed as one of the inner layers. The outer-most layer may be manufactured from any material, including but not limited to a breathable material. The outer-most layer may also be manufactured from any material that would be desirable, including for the purpose of increasing the comfort for the wearer, and enhancing the aesthetics of washable diaper 10.

Figure 8:
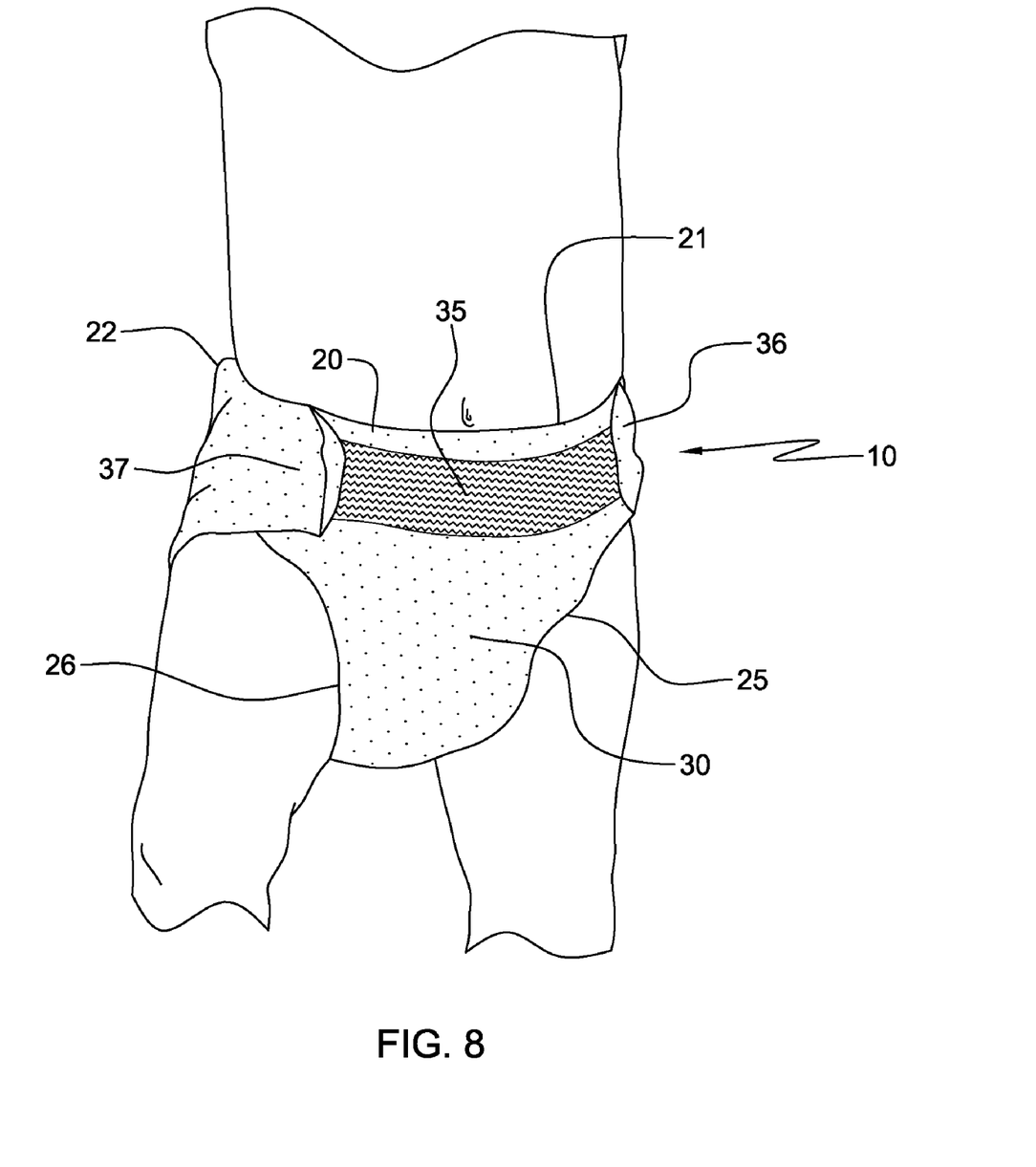
FIG. 8 is a frontal view of the washable diaper of FIG. 1 worn by an infant, in accordance with an aspect of the present invention.
Figure 9:
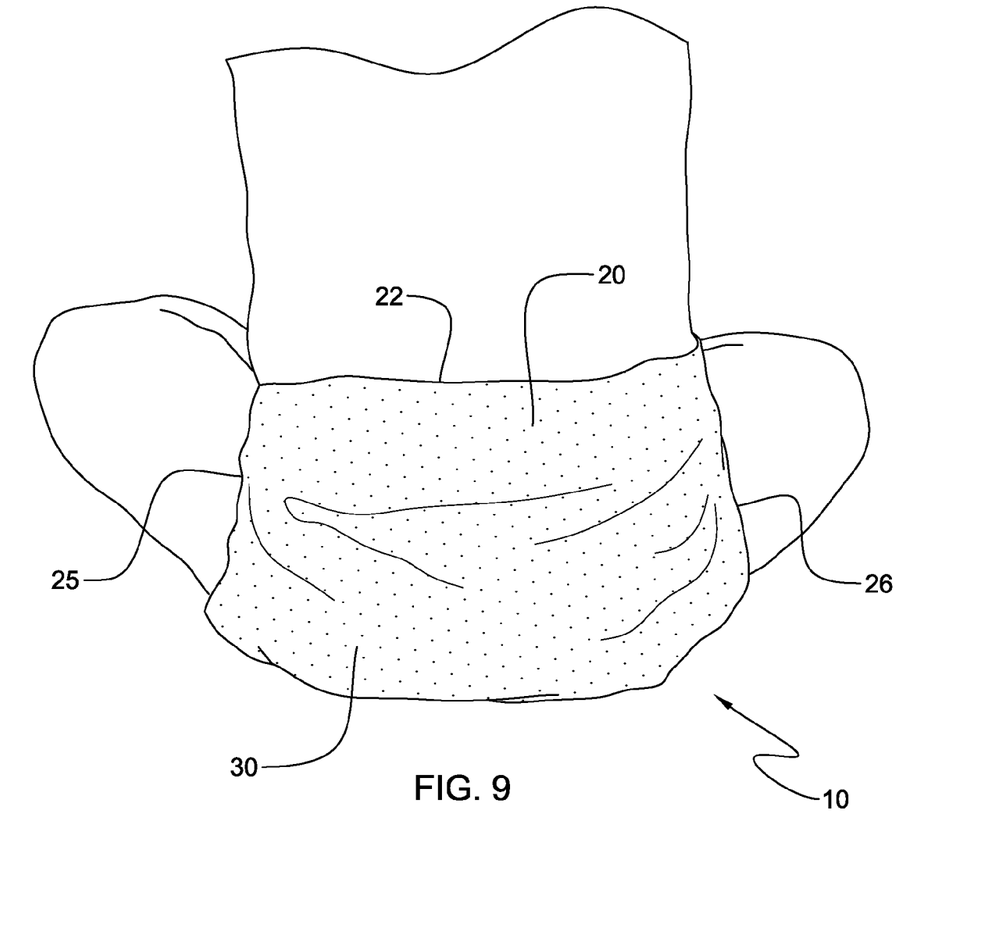
FIG. 9 is a back view of the washable diaper of FIG. 1 worn by an infant, in accordance with an aspect of the present invention.

The fastening mechanisms 33, 34, disposed on extended portions 36, 37 of back end 22 of outer article 20, as depicted in FIGS. 1, 3, 4, 5 and 7, are used to detachably couple to the front of outer article 20, when washable diaper 10 is worn, as shown in FIG. 8. Fastening mechanisms 33, 34 as shown in FIGS. 1, 3, 4, 5 and 7, are hook and loop fasteners, such as the Velcro® brand hook and loop fastener system, but fastening mechanisms 33, 34 may also be one of hook and eye, pin, button, snap button, buckle, or clasp mechanisms.

Figure 2:
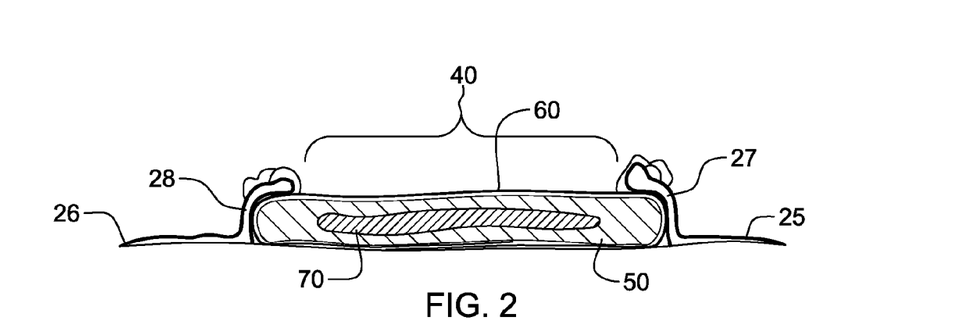
FIG. 2 is an enlarged cross-section view taken along the Line 2-2 of the washable diaper in FIG. 1, in accordance with an aspect of the present invention.

FIG. 2 depicts a cross section of washable diaper 10 of FIG. 1, showing the multiple layers that compose inner liner system 40. Typically, inner liner system 40 is constructed with at least one washable article 50, liner member 60 and at least one absorbent pad 70. Liner member 60 completely surrounds at least one washable article 50. Opposing side barriers 27, 28 further secure inner liner system 40 in outer article 20, so that inner liner system 40 does not shift or move when washable diaper 10 is worn and operate to enhance the containment and absorption of urine and other bodily excrements.

Figure 3:
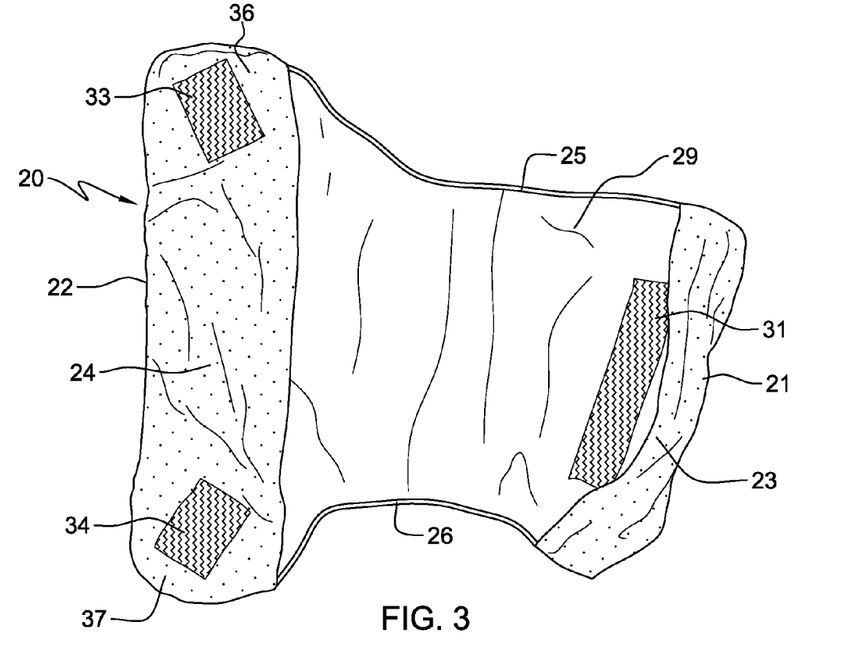
FIG. 3 is a top plan view of another embodiment of the outer article, where the opposing side edges are configured to conform to the body of the wearer of the washable diaper, in accordance with an aspect of the present invention.
Figure 4:
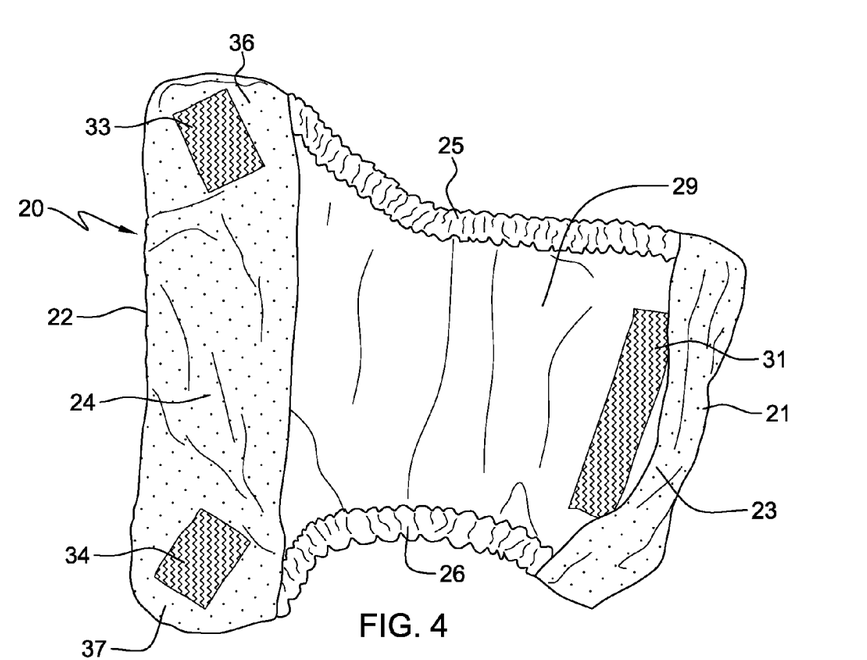
FIG. 4 is a top plan view of another embodiment of the outer article, where the opposing side edges are elasticized to conform to the body of the wearer of the washable diaper, in accordance with an aspect of the present invention.

FIGS. 3 and 4 show additional embodiments of outer article 20 of washable diaper 10. As illustrated in FIGS. 1, 3-5, and 7-9, opposing side edges 25, 26 of outer article 20 are configured to conform to the legs of the wearer of washable diaper 10. Opposing side edges 25, 26 may be elasticized, as shown in FIG. 4, or not, as illustrated in FIG. 3. The contoured configuration of opposing sides 25, 26 of outer article 20 ensures the secure fit of washable diaper 10 and minimizes potential leakage issues. Elasticized opposing side edges 25, 26 as seen in FIG. 4, create a tighter fit on the wearer's legs (see FIG. 8) and provide enhanced protection against leakage.

FIGS. 6A-6C illustrate the method of assembly of liner member 60 and at least one washable article 50. As shown in FIG. 6A, at least one washable article 50 includes opening 53 on first end 51 and opening 54 on second end 52. At least one washable article 50 is usually placed on top of liner member 60 that has first end 61 and second end 62, with three openings 63, 64, 65 on first end 61 and three openings 66, 67, 68 on second end 62. First end 51 of at least one washable article 50 is aligned with first end 61 of liner member 60, and second end 52 of at least one washable article 50 is aligned with second end 62 of liner member 60, so that middle opening 63, 66 of liner member 60 are aligned with openings 53, 54 of at least one washable article 50.

As shown in FIGS. 6B and 6C, the width of liner member 60 is wrapped about at least one washable article 50, so as to wholly surround at least one washable article 50. When liner member 60 is wrapped about at least one washable article 50, openings 64, 65 are aligned with opening 63 on first end of liner member 61 and openings 67, 68 are aligned with opening 66 on second end of liner member 62, as seen in FIG. 6C. Openings 53, 63, 64, 65 are coaxially aligned to represent the composite opening 43 on first end 41 of inner liner system 40 and openings 54, 66, 67, 68 are aligned to represent the composite opening 44 on second end 42 of inner liner system 40.

FIG. 6D depicts an enlarged view of the area identified by the circle noted in FIG. 6C and shows the detailed view of opening 43 on first end 41 of assembled inner liner system 40, that is created by aligning opening 53 on first end 51 of at least one washable article 50 and openings 63, 64, 65 on first end 61 of liner member 60 (shown in FIG. 6C). Composite opening 43 facilitates the ease of detachably coupling inner liner system 40 to outer article 20 using at least one fastening mechanism 31, 32.

FIGS. 8 and 9 show washable diaper 10 being worn by an infant. As seen in FIG. 8, front end 21 of outer article 20 is configured to fit on the front of the infant, with back end 22 of outer article 20 covering the infant's bottom (see FIG. 9). Fastening mechanism 35 is located on outer surface 30 of front end 21 of outer article 20. Extended portions 36, 37 of back end 22 of outer article 20 are wrapped around the infant to detachably couple to front end 21 of outer article 20. Fastening mechanism 35 as shown in FIG. 8 depicts a strip of one part of the hook and loop fastener. Additionally, fastening mechanism 35 may be made of several latching mechanisms including hook and eye, pin, button, snap button or clasp constructs.

Although the preferred embodiments have been depicted and described in detail herein, it will be apparent to those skilled in the relevant art that various modifications, additions, and substitutions may be made without departing from the spirit of the invention, and therefore, those are to be considered to be within the scope of the following claims.

What is claimed is:

1. A washable diaper comprising:
    an outer article configured with a front end, a back end and opposing side edges connecting the front end to the back end, and further comprising an inner surface and an outer surface, wherein at least one fastening mechanism is disposed on the inner surface positioned proximate to at least one of the front end and the back end; and an inner liner system positioned adjacent to the inner surface of the outer article comprising at least one washable article having a first end and a second end, wherein when assembled with the outer article the first end is aligned and detachably coupled with the front end of the outer article and the second end is aligned and detachably coupled with the back end of the outer article, wherein the first end and the second end of the at least one washable article are configured with an opening, and wherein the at least one fastening mechanism of the outer article couples the openings in the first end and the second end of the at least one washable article.

2. The washable diaper of claim 1, wherein the inner liner system further comprises a liner member fabricated from a liquid pervious material, and wherein the liner member is configured to substantially cover the at least one washable article and is positioned adjacent to the inner surface of the outer article upon assembly of the washable diaper.

3. The washable diaper of claim 2, wherein the liner member further comprises a first end and a second end, the first end being positioned proximate to the first end of the at least one washable article and the second end being positioned proximate to the second end of the at least one washable article, wherein when the washable diaper is assembled the first end of the at least one washable article and the first end of the liner member are coupled to the front end of the outer article and the second end of the at least one washable article and the second end of the liner member are coupled to the back end of the outer article.

4. The washable diaper of claim 3, wherein the first end and second end of the liner member are configured with an opening, wherein the at least one fastening mechanism of the outer article couples the openings in the first end and the second end of the liner member.

5. The washable diaper of claim 4, wherein the first end and the second end of the at least one washable article and the first end and second end of the liner member are aligned and are coupled together with the at least one fastening mechanism of the outer article upon assembly of the washable diaper.

6. The washable diaper of claim 2, wherein the liner member comprises a biodegradable material.

7. The washable diaper of claim 1, wherein the front end of the outer article further comprises a front compartment, the front compartment being sized to receive the inner liner system, and wherein the back end of the outer article further comprises a back compartment, the back compartment being sized to receive the inner liner system.

8. The washable diaper of claim 7, wherein the front and back compartments are integral to the outer article and are positioned about normal relative to the opposing side edges.

9. The washable diaper of claim 1, wherein the at least one fastening mechanism further comprises at least one of a hook and loop, a hook and eye, a pin, a button, a snap button, and a clasp in combination with the front and back compartments, the at least one fastening mechanism being configured to detachably couple the inner liner system to the outer article.

10. The washable diaper of claim 1, wherein the opposing side edges are configured to conform to the body of a wearer of the washable diaper.

11. The washable diaper of claim 1, wherein the outer article further comprises side barriers, the side barriers extending from the inner surface and oriented substantially parallel to each other, and the inner liner system positioned fully between the side barriers to inhibit movement of thereof.

12. The washable diaper of claim 11, wherein the side barriers are elasticized to conform to the body of a wearer of the washable diaper.

13. The washable diaper of claim 1, wherein the inner surface of the outer article is liquid impervious.

14. The washable diaper of claim 1, wherein the outer article further comprises at least two layers, wherein one of the at least two layers comprises a liquid impervious material.

15. The washable diaper of claim 1, wherein the inner liner system further comprises at least one absorbent pad, the at least one absorbent pad being removably secured within an opening in the at least one washable article.

16. The washable diaper of claim 1, wherein the at least one fastening mechanism includes at least two components configured to fasten to one another, wherein said two components are disposed on the inner surface of the outer article at each of the front end and the back end, and the two components of each fastening mechanism are spaced from one another in a direction extending from the front end to the back end.

17. The washable diaper of claim 16, wherein the inner liner system further comprises a liner member fabricated from a liquid pervious material having a first end and a second end each configured with an opening, and the liner member is configured to completely surround at least a portion of the at least one washable article such that when the washable diaper is assembled the opening of the first end of the at least one washable article and the opening of the first end of the liner member are adjacent and the opening of the second end of the at least one washable article and the opening of the second end of the liner member are adjacent, wherein the at least one fastening mechanism of the outer article further couples the openings of the first end and the second end of the liner member, and wherein the inner liner system further comprises at least one absorbent pad removably secured within an opening in the at least one washable article.

18. The washable diaper of claim 17, wherein the at least one fastening mechanism of the outer article couples the openings of the at least one washable article and the liner member when the at least two components are fastened to one another through the openings.

19. The washable diaper of claim 18, wherein the outer article deforms to allow the at least two components of the at least one fastening mechanism to be fastened to one another through the openings, and wherein such deformation results in at least the portions of the inner surface proximate the at least two components to lay over one another and form corresponding front and back compartments.

20. The washable diaper of claim 19, wherein the at least two components of the at least one fastening mechanism are positioned on the inner surface of the outer article such that said front and back compartments are sized and shaped to receive therein and inhibit movement of the inner liner system when the two components are fastened to one another through the openings.

21. A diaper comprising:
a reusable outer article configured with a front end, a back end and opposing side edges extending between the front end and the back end, and further comprising an inner surface and an outer surface, wherein disposed on the inner surface of each of the front end and the back end are fastening mechanisms; and
an inner liner comprising;
a washable article having a first end and a second end each configured with an opening, wherein when assembled with the reusable outer article the opening of the first end is aligned and detachably coupled with the fastening mechanism of the front end and the opening of the second end is aligned and detachably coupled with the fastening mechanism of the back end; and a flushable liner member configured to surround the washable article and be positioned adjacent to the inner surface of the reusable outer article upon assembly of the diaper.

22. The diaper of claim 21, wherein the flushable liner member comprises a liquid pervious material.

23. The diaper of claim 21, wherein the flushable liner member further comprises a first end and a second end, the first end being positioned adjacent the first end of the washable article and the second end being positioned adjacent to the second end of the washable article, wherein when the diaper is assembled the first end of the washable article and the first end of the flushable liner member are coupled to the front end of the reusable outer article and the second end of the washable article and the second end of the flushable liner member are coupled to the back end of the reusable outer article.

24. The diaper of claim 23, wherein the first end and second end of the flushable liner member are configured with an opening, wherein the fastening mechanisms couple the openings in the first end and the second end of the flushable liner member into the first and second compartments of the reusable outer article.

25. The diaper of claim 23, wherein the first end and the second end of the washable article and the first end and second end of the flushable liner member are aligned and held by the fastening mechanisms of the front end and back end of the reusable outer article upon assembly of the washable diaper.

26. The diaper of claim 21, wherein the front end of the reusable outer article is configured as a first compartment, the first compartment being sized to receive the inner liner system, and wherein the back end of the reusable outer article is configured as a second compartment, the second compartment being sized to receive the inner liner system.

27. The diaper of claim 26, wherein the first and second compartments are integral to the reusable outer article and positionable about normal relative to the opposing side edges.

28. The diaper of claim 23, wherein the first end and the second end of the flushable liner member are configured with an opening, wherein the fastening mechanisms of the reusable outer article couple the openings in the first end and the second end of the flushable liner member into the first and second compartments of the reusable outer article.

29. The diaper of claim 21, wherein the fastening mechanisms further comprise at least one of a hook and loop, a hook and eye, a pin, a button, a snap button, and a clasp in combination with the first and second compartments, the fastening mechanisms being configured to detachably couple the inner liner system to the reusable outer article.

30. The diaper of claim 21, wherein the reusable outer article further comprises at least two side barriers, the at least two side barriers extending from the inner surface and are positioned proximate to each of the opposing side edges, and the inner liner system positioned fully between the side barriers to inhibit movement of thereof.

31. The diaper of claim 30, wherein the at least two side barriers are elasticized to conform to the body of a wearer of the diaper.

32. The diaper of claim 21, wherein the inner surface comprises a liquid impervious material.

33. The diaper of claim 21, wherein the inner liner system further comprises at least one absorbent pad, the at least one absorbent pad being removably secured within an opening in the washable article.

34. A method of assembling a washable diaper, the method comprising:
    obtaining a reusable outer article having a front end, a back end and opposing side edges connecting the front end to the back end, and an inner surface and an outer surface, wherein disposed on the inner surface of each of the front end and the back end is a fastening mechanism;
    obtaining at least one washable article having a first end and a second end each configured with an opening;
    obtaining a disposable liner member configured to cover the at least one washable article and having a first end and a second end each configured with an opening;
    aligning the opening of the first end of the at least one washable article with the opening of the first end of the liner member and aligning the opening of the second end of the at least one washable article with the opening of the second end of the liner member and wrapping the liner member about the at least one washable article so that the at least one washable article is wholly surrounded, thereby assembling an inner liner system having a first end and a second end each configured with an opening;
    positioning the assembled inner liner system within the reusable outer article; and
    securing the openings of the inner liner system within the reusable outer article with the fastening mechanisms.

35. The method of claim 34, wherein the front end of the reusable outer article being configured as a first compartment, the first compartment having a fastening mechanism disposed therein and being sized to receive the first end of the inner liner system and, wherein the back end of the reusable outer article being configured as a second compartment, the second compartment having a fastening mechanism disposed therein and being sized to receive the second end of the inner liner system.

36. The method of claim 35, wherein the positioning the assembled inner liner system further comprises inserting the first end of the inner liner system into the first compartment and inserting the second end of the inner liner system into the second compartment.

37. The method of claim 36, wherein the first end of the inner liner system is coupled within the first compartment and the second end of the inner liner system is coupled within the second compartment, thereby securing the inner liner system within the reusable outer article.

38. The method of claim 34, wherein the inner surface of the outer article includes opposing side barriers proximate the opposing side edges of the outer article that extend from the inner surface a distance that is greater than the thickness of the inner liner system, and wherein the positioning step includes positioning the assembled inner liner system adjacent to the inner surface of the outer article and fully between the opposing side barriers to inhibit movement of the inner liner system.

* * * * *